United States Patent
Chiapperi et al.

(10) Patent No.: US 8,058,073 B2
(45) Date of Patent: Nov. 15, 2011

(54) IMMUNODIAGNOSTIC TEST CARDS HAVING INDICATING INDICIA

(75) Inventors: Joseph M. Chiapperi, Rochester, NY (US); Mary Kay Golisano, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 12/022,349

(22) Filed: Jan. 30, 2008

(65) Prior Publication Data

US 2009/0191641 A1    Jul. 30, 2009

(51) Int. Cl.
*G01N 21/03* (2006.01)
*G01N 33/86* (2006.01)

(52) U.S. Cl. ............ 436/69; 436/63; 436/164; 436/165; 436/174; 436/809; 435/7.1; 435/7.25; 435/287.1; 435/287.2; 435/288.4; 435/288.7; 422/73; 422/400; 422/401; 422/402; 422/407; 422/430; 422/551; 422/552; 422/559

(58) Field of Classification Search .................... 436/63, 436/69, 164, 165, 174, 809; 435/7.1, 7.25, 435/287.1, 287.2, 288.2, 288.3, 288.4, 288.7; 422/55, 58, 59, 60, 61, 72, 73, 102, 400, 422/401, 402, 407, 409, 430, 547, 548, 551, 422/554, 559, 552
See application file for complete search history.

(56) References Cited

U.S. PATENT DOCUMENTS

| | | | |
|---|---|---|---|
| 3,718,133 A | 2/1973 | Perry et al. | |
| 3,876,376 A | 4/1975 | Bauman et al. | |
| 4,022,576 A | 5/1977 | Parker | |
| 4,234,317 A | 11/1980 | Lucas et al. | |
| 4,391,780 A | 7/1983 | Boris | |
| 4,956,103 A * | 9/1990 | Jessop et al. | 210/787 |
| 4,999,285 A | 3/1991 | Stiso | |
| 5,338,669 A | 8/1994 | Gillies | |
| 5,338,689 A | 8/1994 | Yves et al. | |
| 5,460,940 A | 10/1995 | Yves et al. | |
| 5,512,432 A | 4/1996 | Lapierre et al. | |
| 5,650,068 A * | 7/1997 | Chachowski et al. | 210/518 |
| 5,780,248 A * | 7/1998 | Milchanoski et al. | 435/7.25 |
| 5,824,272 A | 10/1998 | Uchida | |
| 5,830,411 A * | 11/1998 | Martinell Gisper-Sauch | 422/73 |
| 5,863,802 A | 1/1999 | Yves et al. | |

(Continued)

FOREIGN PATENT DOCUMENTS

CH        610197    *   4/1979

(Continued)

OTHER PUBLICATIONS

International Search Report and Written Opinion for International PCT Patent Application No. PCT/US2009/031034; Apr. 3, 2009; 10 Pages.

*Primary Examiner* — Maureen Wallenhorst
(74) *Attorney, Agent, or Firm* — Hiscock & Barclay, LLP

(57) ABSTRACT

An immunodiagnostic test card includes a plurality of transparent chambers wherein each chamber includes a quantity of testing material that combines with a patient sample, when mixed, to produce an agglutination reaction. A plurality of indicia are disposed to aid in the manufacture and determining the usability of the cards prior to test and also in objectively grading the agglutination reactions that are formed or lack of agglutination.

9 Claims, 2 Drawing Sheets

U.S. PATENT DOCUMENTS

| | | | |
|---|---|---|---|
| 5,872,860 A | 2/1999 | Shen et al. | |
| 6,022,700 A | 2/2000 | Monks et al. | |
| 6,114,179 A | 9/2000 | Lapierre et al. | |
| 6,162,399 A | 12/2000 | Martinell Gisper-Sauch | |
| 6,203,706 B1 * | 3/2001 | Schwind et al. | 210/645 |
| 6,261,833 B1 * | 7/2001 | de Oliveira | 435/288.1 |
| 6,974,701 B2 * | 12/2005 | Bouboulis | 436/70 |
| 7,449,329 B2 * | 11/2008 | Hale | 435/288.6 |
| 2002/0045243 A1 | 4/2002 | Laska et al. | |
| 2004/0141882 A1 | 7/2004 | Mimura et al. | |
| 2004/0166551 A1 | 8/2004 | Moulds et al. | |
| 2006/0178578 A1 | 8/2006 | Tribble et al. | |
| 2007/0285804 A1 * | 12/2007 | Raymond et al. | 359/741 |

FOREIGN PATENT DOCUMENTS

| | | |
|---|---|---|
| EP | 0637744 | 11/2001 |
| EP | 1 563 907 A2 | 8/2005 |
| WO | WO 96/00395 | 1/1996 |

* cited by examiner

US 8,058,073 B2

IMMUNODIAGNOSTIC TEST CARDS HAVING INDICATING INDICIA

FIELD OF THE INVENTION

The invention relates to the field of immunodiagnostic testing and more particularly to an immunodiagnostic test card having a plurality of transparent chambers used for testing a patient sample and producing an agglutination reaction, the card further including indicia for objectively grading each reaction.

BACKGROUND OF THE INVENTION

So-called "gel" cards or "bead" cassettes are now commonly used, for example, in the field of immunohematological testing as test elements for blood typing, blood grouping and/or the detection of certain antigens or antibodies. These test elements are commonly defined by a flat planar substrate having a plurality of transparent microtubes or columns that define test chambers. A predetermined quantity of inert bead or gel material is added to each of the microtubes. This inert material may be coated with an antibody or an antigen or provided with a carrier-bound antibody or antigen or with specific reagents. Typically, a foil wrap is used to cover the top of the card or cassette, thereby sealing the contents of each microtube until the time of test. The foil wrap is pierceable or otherwise removed to enable aliquots of patient sample and/or reagents to be added to each of the microtubes, either manually or in an automated apparatus. The sample is incubated and then mixed into the contents of the test chambers by centrifugation. During centrifugation, red blood cells (RBCs) in each reaction chamber are pulled into the gel column. Agglutinated RBCs are too large to pass through the gel matrix, depending on the size of the agglutinates, while unagglutinized RBCs will pass easily through the gel and pellet at the bottom of the chamber.

A grading system is used with regard to a resulting agglutination reaction with regard to RBC agglutinates that are trapped anywhere in the gel column. Positive reactions can be graded from 0 to 4+. More specifically, a 4+ reaction is indicated by a solid band of RBCs on top of the gel. A 3+ reaction displays agglutinated RBCs in the upper half of the gel column. A 2+ column is characterized by RBC agglutinates dispersed throughout the length of the column. A 1+ column is indicated by RBC agglutinates mainly in the lower half of the gel column with some agglutinated RBCs being pelleted at the bottom of the column. Negative (0) reactions are characterized by a pellet of RBCs on the bottom of the microtube with no agglutinates along the length of the column. In the course of testing, the resulting reaction can be highly positive; that is, all or most of the formed agglutinate is disposed above the inert material layer, or highly negative; that is, in which no agglutination results and all of the cells is located at the bottom of the microtube as a pellet. Gradients of these reactions are also produced wherein formed agglutinate can be distributed anywhere throughout the gel/bead matrix and wherein this distribution must be graded as being either highly or weakly positive.

The grading of agglutination reactions using immunodiagnostic test cards, such as those manufactured by DiaMed, Inc. and Micro-Typing Systems, Inc., among others, is somewhat difficult, for agglutination reactions, for example that are not highly positive or highly negative. Among the most difficult to grade are those reactions between a 4+ and a 3+ reaction and between a 1+ and a negative (0) reaction. Ultimately, such determination becomes highly user-dependent especially when the test cards or cassettes are read manually, making the process extremely subjective as to the position of agglutinates in the column, and requiring users who have significant experience perform the reading operation in order to obtain consistent results. In addition and because the card or cassette surface is typically relatively smooth throughout, it is often difficult for image processing algorithms of automated apparatus to accurately locate the exact position of the column(s) in the field of view. Exemplary image processing algorithms are described, for example, in EP Patent 0 637 744 to Shen et al. This perceived difficulty drives additional cost into the design of a suitable illumination system. Having an incorrect determination can produce dire or fatal consequences; for example in instances for determining proper blood samples for transfusion.

The manufacturing of test elements as described above is also dependent upon adding the proper amount of inert material into each of the microtubes. Though this manufacturing process can be automated, errors can still result. For example, a dispensing mechanism can be improperly positioned relative to the test element or tolerance buildup issues may have occurred in the manufacture of a card or cassette, requiring in-process manufacturing checks for fill volume and label placement. If an improper amount of inert material is provided in any of the microtubes, the results as graded from the resulting agglutination reaction may not be accurate. For those reasons, among others, it is desirable to improve the design of immunodiagnostic test cards and cassettes.

SUMMARY OF THE INVENTION

Therefore and according to one aspect, there is described a method of manufacturing an immunodiagnostic test element, and more specifically a test card or cassette. The manufacturing method comprises the steps of: forming a planar substrate, said substrate including at least one supported transparent well; providing a plurality of indicia on said at least one transparent well; and adding a volume of testing material to the interior of said at least one well. The indicia is used according to this method to indicate a proper amount of material has been added to each of the reaction wells. This indicia can be added by integrally molding it into the transparent wells or the card/cassette itself or by other means in which the indicia can be located directly on the columns or adjacent thereto. The indicia can be in the form of a plurality of linearly spaced lines or other forms can be used to provide the user/manufacturer with visual indicators.

According to another aspect, there is described a method for grading an agglutination reaction using an immunodiagnostic test card, said test card including at least one column retaining a test material, the method comprising the steps of: providing a set of indicia relative to each said at least one column of a said test card; adding patient sample and possibly reagent to each column, mixing the patient sample with the contents of the column to produce an agglutination reaction between the patient sample and said test material, and grading the reaction by visually noting the position of formed agglutinates within said column relative to said indicia. This indicia can be provided, according to one embodiment, directly to the external surfaces of each column to provide a measurement scale or visual reference for the user or for an automated system. The indicia can take one of several forms; for example, indicator marks can be provided at predetermined locations along the column, either directly within the column or adjacent thereto. The indicator marks can be molded directly into the column or alternatively can be separately applied, such as by printing, laser etching or other suitable means to provide a more accurate gradation as to the position of formed agglutinates within the column. The indicator marks can be linear in shape or can assume one of several convenient forms wherein these marks can be clear or alternatively be colored in order to better visualize the position of agglutinate relative to a contained test material matrix. In another example, the indicia can include one or more raised or depressed marks, creating distinct relief from the smooth card surface that is more easily discerned by the illumination system of an automated machine vision apparatus as a visual datum, for example, using lines of known length and separation. This indicia assists the image processing algorithms of an automated apparatus to locate or "find" the columns of the card in the visual field. The image processing algorithms can then accurately determine the position of agglutinates relative to the indicia and properly calculate a reaction grade. The indicia as raised marks also breaks off the smooth surface of the card and provides a transition point for light emitted from the illumination system of the apparatus to reflect. This reflection will be more easily observed as an edge by the image processing software of the apparatus, thereby reducing the cost and complexity of the illumination system.

One advantage realized by the test card design described herein is that subjectivity and "skill" in the reading of test elements, and particularly manual reading of same, is virtually eliminated. That is, manual reading of a test element is improved by providing a reliable visual reference and measurement scale, thereby producing improved and repeatable results and accuracy.

Another advantage is that test cards and cassettes can be manufactured more efficiently than previously known versions. The indicator marks or other indicia that is provided can be used with either in-process visual or machine vision systems to more easily determine the accuracy of the fill volume of gel or beads (or other suspended matrix) in the columns. The indicator marks or other indicia also provide a consistent datum on the card or test cassette to assist in process visual systems to determine if product labels have been correctly positioned on the test card. In addition, incorporation of indicia as described herein can also be used by automated apparatus in order to reject cards in advance that do not include the indicia as a measure of quality assurance.

Yet another advantage is that the indicia used can also provide an indication relating to evaporation of contained test materials following manufacture of the test element that can readily deduced, thereby better insuring the quality of tests that are conducted.

These and other features and advantages will be readily apparent from the following Detailed Description, which should be read in conjunction with the accompanying drawings.

DETAILED DESCRIPTION

The following description relates to an improved immunodiagnostic test card or cassette that includes indicia to enable a user and/or an automated apparatus to better visualize and grade sample agglutination reactions for purposes of blood bank applications such as antibody screening and identification, ABO blood grouping and Rh phenotyping, reverse serum grouping, direct antiglobulin testing and antigen typing, among other uses. This indicia also provide a means to more effectively control and maintain aspects relating to the manufacture of an immunodiagnostic test card or cassette. It will be readily apparent to those of sufficient skill that there are available variations and modifications that are within the inventive aspects discussed herein. For example and in the examples described herein, the patient sample tested is red blood cells (RBCs) or sera, though the patient sample can include other body fluids, such as but not limited to amniotic fluid, spinal fluid, urine, plasma, and serum or any other body fluid that is capable of producing an agglutination reaction. In addition, several terms are used throughout in order to provide a suitable frame of reference with regard to the accompanying drawings. These terms are not intended to be limiting of the concepts covered by the claims of this application, except where so specifically indicated.

Figure 1:
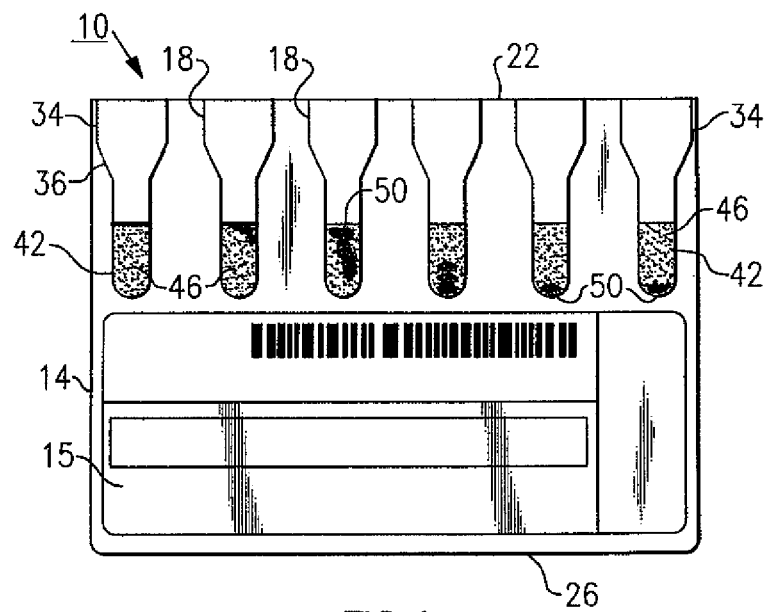
FIG. 1 depicts a prior art immunodiagnostic test card following testing thereof, the card including several test chambers or columns, wherein each of the columns provide indication of an agglutination reaction in relation to a patient sample.

Referring to FIG. 1 and for purposes of background, there is shown a prior art immunodiagnostic test element, in this case a gel card 10. The gel card 10 shown is defined by a substantially flat planar member 14 or substrate that further includes a plurality of microtubes or columns 18, each being arranged in parallel and in a vertical orientation relative to top and bottom surfaces 22, 26 of the test card. The material of the gel card 10 and the supported microtubes 18 themselves is not necessarily critical. In one embodiment, the microtubes 18 are formed from a transparent plastic material such as polyethylene, polystyrene or PVC and are integrally manufactured by means of blister packaging while the substrate is manufactured from polystyrene or a similar structural material. Each of the microtubes 18 are defined by a substantially cylindrical well 30 that includes an open-ended upper cylindrical portion 34 extending downwardly from the top surface 22 of the card 10 to a closed lower cylindrical portion 42. The upper cylindrical portion 34 has a somewhat constant diameter that extends to an inwardly tapering or transitional portion 36 intermediate the upper and lower portions wherein the lower portion 42 includes a diameter that is smaller than that of the upper portion. The immunodiagnostic gel card 10 depicted in FIG. 1 includes a total of six (6) vertically disposed columns (microtubes), though this number can be suitably varied depending on the test to be performed.

The gel card 10 further includes a product label 15 that is adhesively attached to one facing side of the card, the label including relevant information such as the type of card, lot information and expiration date and having both visual readable and machine readable sections, such as bar-coded section 16.

Provided within each of the defined test chambers 30 is a quantity of test material 46 that produces a reaction with the patient sample and provides a means for separation of agglutinates. In the specific gel card illustrated in FIG. 1, this column is approximately 15 mm long and 4 mm wide. Each column contains a dextran acrylamide gel prepared in a buffer solution, such as LISS or saline. The gels may also contain other elements: preservatives such as sodium azide, sedimenting agents such as bovine serum albumin, and in some cases, specific reagents such as anti-IgG or other RBC-specific antisera (ABO and D). In the instance when reagents are added, they are dispersed throughout the length of the gel column. As such, the gel column is approximately 75 percent packed gel and 25 percent liquid. The testing material 46 is typically provided by the manufacturer wherein a pierceable foil wrap is used to cover the top side of the card and each of the microtubes 18, sealing the contents. In an automated apparatus, the foil wrap is pierced and patient sample and possibly reagents are added and then the test card is centrifuged to accelerate an agglutination reaction.

As noted, this test element 10 is exemplary of those that include at least one supported column that includes a test material and is capable of producing an agglutination reaction with regard to a sample. To that end examples of test cards or cassettes, including features relating to the inert testing material and related test processing, are described in greater detail in U.S. Pat. Nos. 5,338,669, 5,460,940, 5,512,432, and 6,114,179, the entire contents of which are herein incorporated by reference. The reaction can occur in the top of the test chamber 34 or on the lower portion 42 wherein the strength of reaction is measured by the position of the formed agglutinates in the gel column or by the lack of agglutinates.

Following testing of a test card, such as described by the foregoing patents and as depicted in FIG. 1, there are various grades of agglutination reactions ranging between a strong positive reaction and a strong negative reaction, with gradients therebetween. As noted previously, a grading system is used with regard to a resulting agglutination reaction with regard to RBC agglutinates, labeled generally by reference numeral 50, that are trapped anywhere in the gel column. Positive reactions can be graded from 0 to 4+. More specifically, a 4+ reaction is indicated by a solid band of RBCs on top of the gel. A 3+ reaction displays agglutinated RBCs in the upper half of the gel column. A 2+ column is characterized by RBC agglutinates dispersed throughout the length of the column. A 1+ column is indicated by RBC agglutinates mainly in the lower half of the gel column with some agglutinated RBCs 50 being pelleted at the bottom of the column. Negative (0) reactions are characterized by a pellet of RBCs on the bottom of the microtube with no agglutinates along the length of the column. In the course of testing, the resulting reaction can be highly positive; that is, all or most of the formed agglutinate is disposed above the inert material layer, or highly negative; that is, in which no agglutination results and all of the cells is located at the bottom of the microtube as a pellet Determinations of the separate reactions can be made visually by one or more persons or through machine vision such as provided on various automated apparatus, such as the ProVue@ manufactured by Ortho-Clinical Diagnostics, Inc., using the above-depicted test card 10, the machine vision system including an illumination system.

Figure 2:
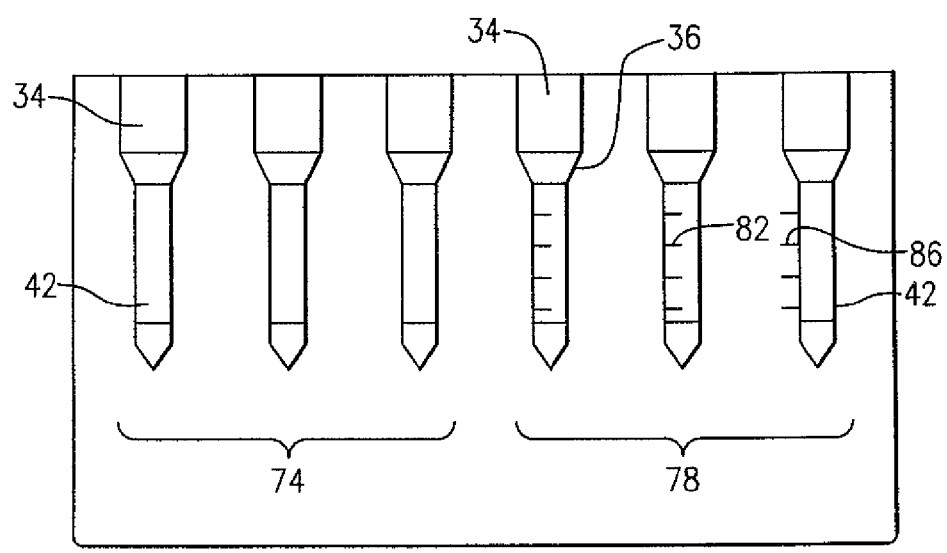
FIG. 2 is a pictorial representation of a portion of the prior art test card of FIG. 1, as contrasted with columns of a test element design that is made in accordance with a first embodiment.

Referring to FIG. 2, there is shown an immunodiagnostic test card 70 that includes for comparison purposes a first series of supported columns 74 made in accordance with the prior art and a second series of supported columns 78 having indicia in the form of indicator marks 82. The marks 82 can be provided for the purpose of defining reaction grades as described in greater detail in a following section. According to this specific embodiment, the supported columns and test substrate are each made from a moldable plastic material such as polystyrene, PVC, or polyethylene. Each of the columns 74 and 78 are similarly constructed as described with regard to FIG. 1 including an upper, open-ended cylindrical portion 34, a transitional intermediate portion 36 and a closed lower cylindrical portion 42. The indicator marks 82 according to this embodiment are specifically formed with each of the plastic columns 74 and are molded therein, though the marks can otherwise be added, for example, by laser etching, printing or other similar means. The indicia according to this embodiment are a set of parallel horizontal lines 82 having a known separation therebetween and having a predetermined length extending across a portion of the width of each column. This indicia can alternatively be provided immediately adjacent each of the columns, for example, as shown by a similar set of horizontal spaced lines shown as 86. It will be readily apparent that other forms of indicia having various shapes and lengths can be used linearly spaced "tick marks", though other indicia such as those having trapezoidal, circles, shouldered or other form or shape can be utilized. Additionally, at least some of the indicia can be colored to further permit recognition, either visually or by machine vision.

In addition and according to this embodiment, each of the lines 82, 86 are raised above the column surface so as to create distinct relief from the smooth card surface that is more easily discerned by the illumination system of an automated machine vision apparatus (not shown) as a visual datum, for example, using the herein described lines of known length and separation. This indicia assists the image processing algorithms of an automated apparatus locate the columns of the card in the visual field. Moreover, the raised marks also breaks off the smooth surface of the card and provides a transition point for light emitted from the illumination system of the apparatus to reflect from. This reflection will be more easily observed as an edge by the image processing software of the automated apparatus. Alternatively, the lines 82 and 86 could be recessed or depressed in relation to the surrounding column surface or that of the substrate.

Figure 3:
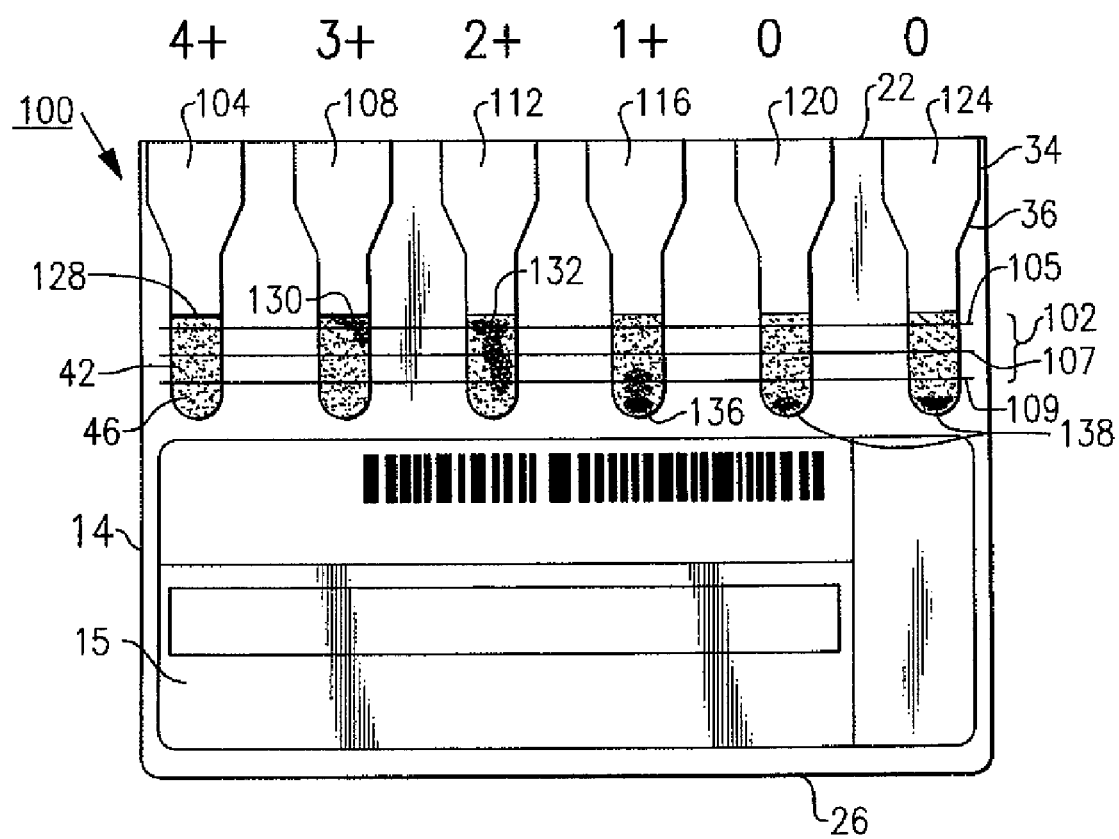
FIG. 3 depicts an immunodiagnostic test element made in accordance with a second embodiment following testing wherein agglutination reactions formed within columns of the test element can be graded by way of indicia provided on the test element.

A test card 100 made in accordance with a second embodiment is depicted in FIG. 3. For purposes of this discussion, it should be noted that similar parts are labeled with the same reference numerals. The test card 100 is defined by a planar substrate 14 that supports a plurality of microtubes 18. The microtubes 18 like the preceding commonly include an upper cylindrical portion 34, an inwardly tapering transitional portion 36 and a lower cylindrical portion 42, the latter defining a set of test columns representative of those provided on the immunodiagnostic test card of FIG. 1, but further including indicia in the form of indicator marks. According to this embodiment, the indicia are represented by a series of horizontal evenly spaced parallel lines 102, each of the lines being raised and provided on the exterior surface of each of the columns and planar substrate 14. According to this embodiment, the lines 102 are formed by laser etching though can be added through other suitable means. Each of the indicator lines 102 are evenly spaced with respect to one another and define separation or gradation zones therebetween for purposes of either describing or grading an agglutination reaction involving at least one column of the test card or for purposes of manufacture of the card for purposes of adding gel material thereto and providing a datum or reference for that purpose. In addition, the use of indicator marks, such as those described herein, can also provide an indication following manufacture and prior to use, as to whether there have been evaporative effects as to the contents of any of the microtubes. It has been determined that in spite of the foil wrap that evaporation can still occur over time and therefore the indicator marks provide yet another function. The test card 100 illustrated includes six (6) microtubes 18, thereby defining a total of 6 test columns.

A working example is herein described for purposes of clarity for purposes of performing a direct antiglobulin test (DAT) for the detection of blood cells that are coated with IgG and/or complement due to an in vivo sensitization using the test card 100 of FIG. 3. The test is performed using an ID-MTS gel card manufactured by Micro Typing Systems, Inc. For purposes of this test card and according to this example, five ml of Sephacryl, 200 Gel (Pharmacia) is washed twice in saline solution. The gel particles have a diameter of between about 10 and 200 microns. After centrifuging, (5 min, 1250× g) the supernatant is discarded and the sediment is filled up to 4.5 ml with isotonic imidazol buffer (0.014 mol/l imidazol 0.085% NaCl), pH 7.6. Polyspecific Anti-Human Globulin (Anti-IgG, -C3d) is then added to the above suspension and is used for detecting IgG and/or complement bound to patient red blood cells. The suspension is mixed well and is ready for use in this form. Approximately 35 µl of the above solution is then placed in each of the test chambers of the gel card, the latter being made from polyethylene (the micro-tubes of this example being ET-29 mM, sold by Milana SA, Geneva, Switzerland). The inert particles settle to the bottom of each microtube 18 within a few minutes.

In terms of the DAT test procedure and using a gel microtube 18 that contains Anti-IgG, -C3d as described and 50 µl of suspended RBCs at an 0.8 percent concentration is added to the reaction chamber of the microtube. The mixture is centrifuged for 10 min at approximately 70×g. During centrifigation, RBCs in the reaction chamber are pulled into the gel column. Sensitized RBCs will pass through the upper part of the gel column and agglutinate in the presence of the anti-IgG. Agglutinated RBCs are too large to pass through the gel matrix and therefore these agglutinates become trapped at various places along the length of the gel column, depending on the size of the agglutinates. Unagglutinated RBCs slip easily through the gel column and pellet at the bottom of the microtube.

The test card 100 depicted includes columns that permit direct Coombs testing, as described above, and control sampling using the six (6) columns. Only the direct AntiGlobulin Test (DAT) has been described herein. More specifically and according to the test card depicted in FIG. 3, the columns of the test card 100 have undergone testing and the resulting agglutination reactions can be graded, using the indicia. As previously noted, each of the horizontally disposed indicator lines 102 are spaced from one another, thereby forming a plurality of gradation or separation zones that can be utilized either through direct vision by a user or through machine vision, such as described in EP 0637744B1, the entire contents of which are herein incorporated by reference. For purposes of this discussion, the position of the agglutinates and hence the reaction in each gel column can be easily graded based on their relative position. Nominally, the reactions can be scaled as follows: First, the presence of all agglutinates above the uppermost indicator line provides the indication of a strong positive reaction and a grade of 4+. On the other hand, the formation of a pellet at the bottom of a microtube with no formed agglutinates anywhere in the column indicates a negative reaction (0) has occurred. Each of the foregoing are usually fairly easy to associate. By virtue of the indicator lines 102, scaling in addition can be established. More specifically, the presence of formed agglutinates in the zone between the uppermost indicator line 105 and the center indicator line 107 in spite of the formation of agglutinates above the gel layer, provides an indication that a weaker positive reaction has taken place. Likewise, the presence of any agglutinate in the zone between the lowermost indicator line 109 and the center indicator line 107, despite the formation of a pellet at the bottom of the microtube indicates that a very weak positive reaction has occurred.

More specifically and by way of the example test card in FIG. 3 and beginning from the far left side of the card and in microtube 104, it is apparent that a strong positive reaction has taken place wherein the formed agglutinates 128 are entirely formed above the inert material 46 as well as above the uppermost indicator line 105. The lack of any agglutinates below the uppermost indicator line provides an indication of a strongly positive 4+ reaction grade. In the adjacent second column 108, and though a portion of the formed agglutinates 130 are located above the uppermost indicator line 105, another portion is found in the zone formed between the uppermost and the center indicator lines 105, 107. As noted above, the latter presence of agglutinates indicates that reaction that is more weakly positive than that in the foregoing first column has occurred. As a result, this reaction has a grade of 3+. In the third adjacent column 112, formed agglutinates 132 are spread or dispersed across each of the zones defined by the three indicator lines 105, 107, 109. This general dispersion indicates the existence of a weaker reaction than that indicated in the second column 108 and defines a 2+ reaction. In the fourth column 116, formed agglutinates 136 are solely found in the zone defined between the lowest indicator line 109 and the center indicator line 107. No agglutinates are found above the center indicator line 107. The presence of agglutinates 136 in this zone indicates a 1+ reaction. Finally and in the fifth and sixth columns 120, 124, no formed agglutinates have formed with a pellet of cells 138 settling at the bottom of each column below the lowermost indicator line 109, thereby indicating that a negative or (0) reaction has occurred in each instance.

The indicia used are lines, raised or otherwise, as depicted according to FIGS. 2 and 3. However and as previously noted, it will be readily apparent that other forms or types of indicia can be used, including, but not limited to circles, trapezoids, square shouldered lines, and the like. In addition, this indicia can be clear or alternatively colored in order to accent between agglutinate and the test matrix and can also be formed either above or below the surrounding surface.

Indicia, such as shown in FIGS. 2 and 3, can also be used in terms of the manufacture of immunodiagnostic test cards. By placing indicia in relation to each transparent microtube, a determination can be made as to the quantity of inert gel, bead or similar material being added to the confines of each test chamber as well as other manufacturing processes, for example, the proper placement of a product label 15 or the placement of the coded section 16 of the label.

PARTS LIST FOR FIGS. 1-3

10 immunodiagnostic test card
14 flat planar member or substrate
15 label
16 machine-coded section
18 microtubes
22 top surface, card
26 bottom surface, card
30 cylindrical well or chamber
34 upper cylindrical portion
36 inwardly tapering or transitional portion
42 lower cylindrical portion
46 material, test
50 agglutinates
70 immunodiagnostic test card
74 columns
78 columns
82 indicator marks
86 indicator marks 100 test card
102 indicator lines
104 first column
105 uppermost indicator line
107 center indicator line
108 second column
109 lowermost indicator line
112 third column
116 fourth column
120 fifth column
124 sixth column
128 formed agglutinate
130 formed agglutinate
132 formed agglutinate
136 formed agglutinate
138 pellet Though the concepts that have been described relate to specific embodiments and related methods, it will be readily apparent to those of sufficient skill that there are variations and modifications embodying the inventive ambits as recited in the following claims. As noted, the tests and test elements described herein are merely exemplary as literally any form of blood banking or other serological and sample testing can be similarly conducted embodying the concepts described herein using any test element capable of forming an agglutination reaction. In addition, the lines defined described above are also exemplary, wherein the spacing and configuration can suitably be varied, for example, depending on the form of test and design of the test chamber used.

The invention claimed is:

1. A method for manufacturing and using an immunodiagnostic test card, said immunodiagnostic test card including at least one transparent column, said at least one transparent column initially containing at least one of a quantity of beads and gel material capable of trapping agglutinates produced by an agglutination reaction, said method comprising the steps of:
    providing indicia relative to said at least one transparent column of said immunodiagnostic test card, said indicia including a set of at least three parallel spaced markings in relation to said beads or gel material in said at least one transparent column, wherein said set of parallel spaced markings collectively define a grading scale defined by a plurality of visible adjacent grading zones with regard to agglutinates formed from an agglutination reaction;
    filling said at least one transparent column with at least one of beads and gel material wherein said indicia is used as a datum for determining the fill accuracy of said material;
    adding a quantity of patient sample to said at least one transparent column;
    mixing the patient sample with the contents of said at least one transparent column to produce an agglutination reaction; and
    assigning a grade to the agglutination reaction by visually detecting the presence or absence of agglutinates relative to said set of spaced markings, wherein said grading scale is defined between 0, indicative of a very strong negative reaction in which no agglutinates are formed and a pellet of cells are present below a lowermost visible grading zone and 4+, indicative of a very strong positive reaction in which all of the formed agglutinates are present above an uppermost visible grading zone based on the relative position of the formed agglutinates within the beads or gel material following said mixing step, said grade assigning step including the step of determining the position of the majority of formed agglutinates within a visible grading zone of said column and grading the reaction based on the location of said majority of formed agglutinates.

2. A method as recited in claim 1, wherein said at least one transparent column is made from a moldable plastic material, said method including the step of molding said indicia directly into said at least one transparent column.

3. A method as recited in claim 2, wherein said indicia includes at least one raised or depressed surface, said method including the step of detecting said at least one raised or depressed surface by machine vision.

4. A method as recited in claim 3, wherein said indicia includes a plurality of raised or depressed surfaces defined by a series of parallel spaced lines having separations therebetween, said lines being disposed on said at least one transparent column in relation thereto to define said grading zones such that the position of formed agglutinates within one or more of said grading zones defines a grade of reaction for said assigning step.

5. A method as recited in claim 1, including the step of providing said indicia adjacent to said at least one transparent column.

6. A method as recited in claim 1, including the step of at least one of etching and printing said indicia onto said card.

7. A method as recited in claim 1, further including the step of inspecting the level of said gel or bead material in said at least one transparent column relative to said indicia prior to use of said card to verify whether any evaporative effects of said material have occurred.

8. A method as recited in claim 1, further including the step of utilizing at least one of said indicia as a datum for a label attached to said test card.

9. An immunodiagnostic test card comprising:
    a planar substrate;
    a plurality of transparent columns supported by said planar substrate, each of said transparent columns retaining a quantity of one of beads and gel material for trapping formed agglutinates from an agglutination reaction created by a patient sample and at least one reagent, each of said transparent columns further including a set of at least three reaction grade markings disposed in relation to the beads and gel material, wherein each of said plurality of transparent columns is initially filled with said quantity of one of beads and gel material wherein said markings are used as a datum to determine the fill accuracy of said material, said markings each being spaced in relation to one another to create a plurality of adjacent visible grading zones to permit the assignment of a reaction grade based on the position of the majority of formed agglutinates in each transparent column, said visible grading zones being used collectively in order to assign a reaction grade based on the position of the majority of formed agglutinates with respect to one of said visible grading zones.

* * * * *